US012632703B2

(12) United States Patent
Pang et al.

(10) Patent No.: US 12,632,703 B2
(45) Date of Patent: May 19, 2026

(54) GENERALIZABLE MACHINE LEARNING ALGORITHMS FOR FLASH CALCULATIONS

(71) Applicant: Schlumberger Technology Corporation, Sugar Land, TX (US)

(72) Inventors: John Pang, Singapore (SG); John Godlewski, Menlo Park, CA (US); Alfredo De La Fuente, New York, NY (US); Suhas Suresha, Menlo Park, CA (US); Soumya Gupta, Santa Clara, CA (US); Prasad Bhagwat, Santa Clara, CA (US); Jose Celaya Galvan, Sunnyvale, CA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 642 days.

(21) Appl. No.: 18/245,772

(22) PCT Filed: Sep. 14, 2021

(86) PCT No.: PCT/US2021/071444
§ 371 (c)(1),
(2) Date: Mar. 17, 2023

(87) PCT Pub. No.: WO2022/061331
PCT Pub. Date: Mar. 24, 2022

(65) Prior Publication Data
US 2023/0394283 A1     Dec. 7, 2023

Related U.S. Application Data

(60) Provisional application No. 62/706,922, filed on Sep. 18, 2020.

(51) Int. Cl.
*G06N 3/0455*     (2023.01)
*E21B 41/00*     (2006.01)
(Continued)

(52) U.S. Cl.
CPC ........... *G06N 3/0455* (2023.01); *E21B 41/00* (2013.01); *G01N 33/2823* (2013.01); *G06N 3/09* (2023.01); *E21B 2200/20* (2020.05)

(58) Field of Classification Search
None
See application file for complete search history.

(56) References Cited

U.S. PATENT DOCUMENTS

| | | |
|---|---|---|
| 2018/0045046 A1 | 2/2018 | Stone et al. |
| 2018/0142543 A1 | 5/2018 | Gupta et al. |

(Continued)

OTHER PUBLICATIONS

Garganis, V. et al., "Machine Learning Methods to Speed up Compositional Reservoir Simulation", SPE 154505, presented at the EAGE Annual Conference, Copenhagen, Denmark, 2012, 11 pages.
(Continued)

*Primary Examiner* — Shelby A Turner
*Assistant Examiner* — Cynthia L Davis
(74) *Attorney, Agent, or Firm* — Kyle R. Miiller

(57) ABSTRACT

A method may include obtaining input data including an environmental condition and chemical properties of input components of an input fluid mixture, encoding, by an encoder machine learning model, the input data to obtain encoded input data, and receiving, by an aggregator function and from the encoder machine learning model, the encoded input data ordered in a sequence corresponding to an order of the input components. The method may further include aggregating, by the aggregator function, the encoded input data to obtain aggregated input data. The aggregated input data may be independent of the sequence. The method may
(Continued)

further include decoding, by a decoder machine learning model, the aggregated input data to obtain output data including a phase for an output mixture, and presenting the output data.

17 Claims, 8 Drawing Sheets

(51) Int. Cl.
| | | |
|---|---|---|
| *G01N 33/28* | (2006.01) | |
| *G06N 3/09* | (2023.01) | |

(56) References Cited

U.S. PATENT DOCUMENTS

| | | | |
|---|---|---|---|
| 2019/0095792 A1 | 3/2019 | Kashinath | |
| 2019/0227191 A1 | 7/2019 | Raman | |
| 2020/0242812 A1* | 7/2020 | Rehfeld | ............... G06N 3/0464 |
| 2021/0097401 A1* | 4/2021 | Ramalho | .............. G06N 3/0464 |

OTHER PUBLICATIONS

Wang, K. et al., "Artificial neural network assisted two-phase flash calculations in isothermal and thermal compositional simulations", Fluid Phase Equilibria 486, 2019, pp. 59-79.

Li, Y. et al., "Acceleration of the NVT-flash calculation for multicomponent mixtures using deep neural network models", 2019, arXiv:1901.09380v1, 26 pages.

Baltrusaitis, T. et al., "Multimodal Machine Learning: A Survey and Taxonomy", arXIV:1705.09406v2, 2017, 20 pages.

Zaheer, M. et al., "Deep sets", 2018, arXiv:1703.06114v3, 29 pages.

Li, Y et al., "Accelerating Flash Calculation through Deep Learning Methods", arXiv:1809.07311v1, Sep. 19, 2018, 16 pages.

Search Report and Written Opinion of International Patent Application No. PCT/US2021/071444 dated Dec. 28, 2021, 9 pages.

Gaganis, V. et al., "An integrated approach for rapid phase behavior calculations in compositional modeling", Journal of Petroleum Science and Engineering, 2014, 118, pp. 74-87.

Extended Search Report issued in European Patent Application No. 21870443.5 dated Sep. 12, 2024, 10 pages.

* cited by examiner

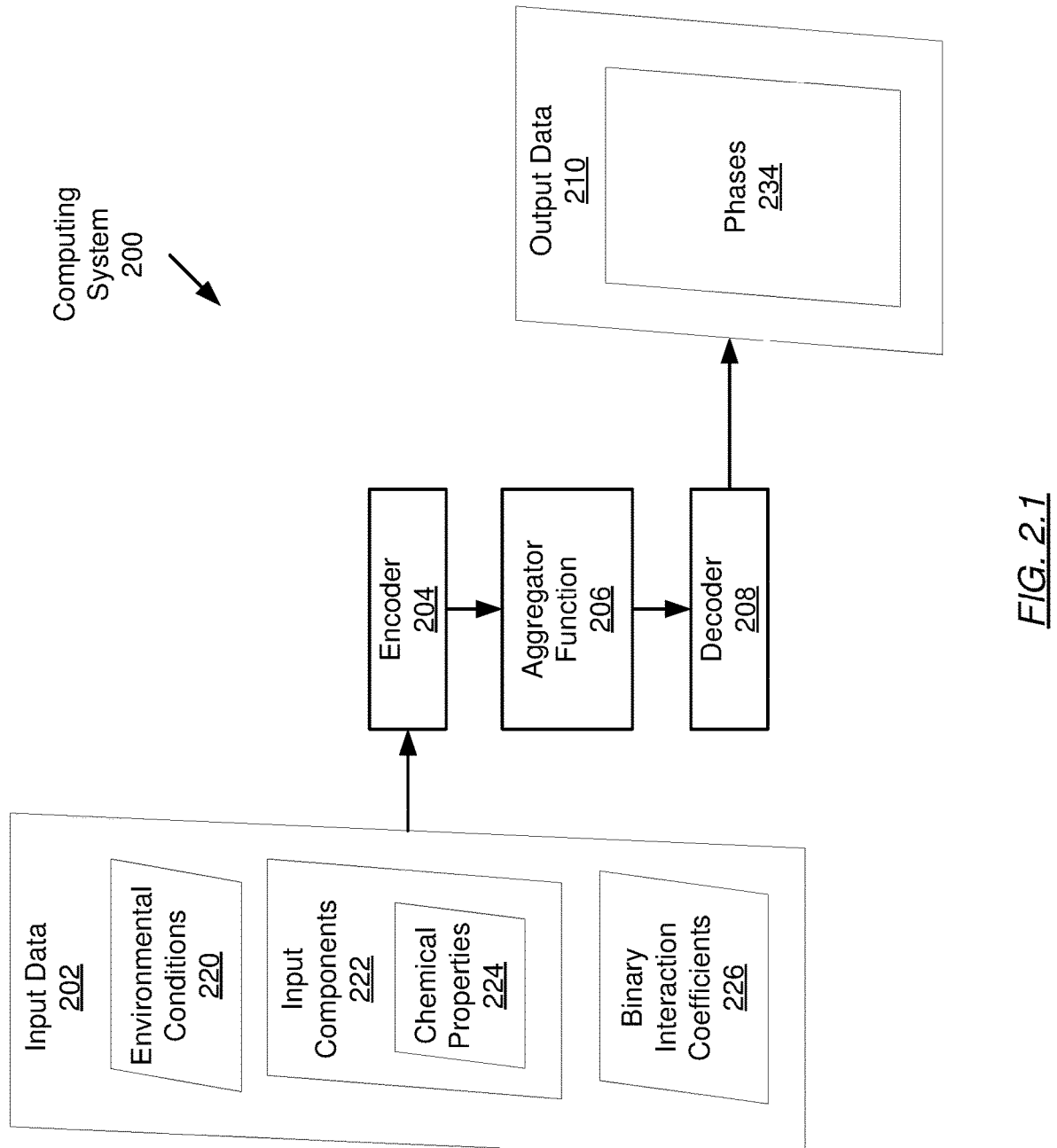
*FIG. 2.1*

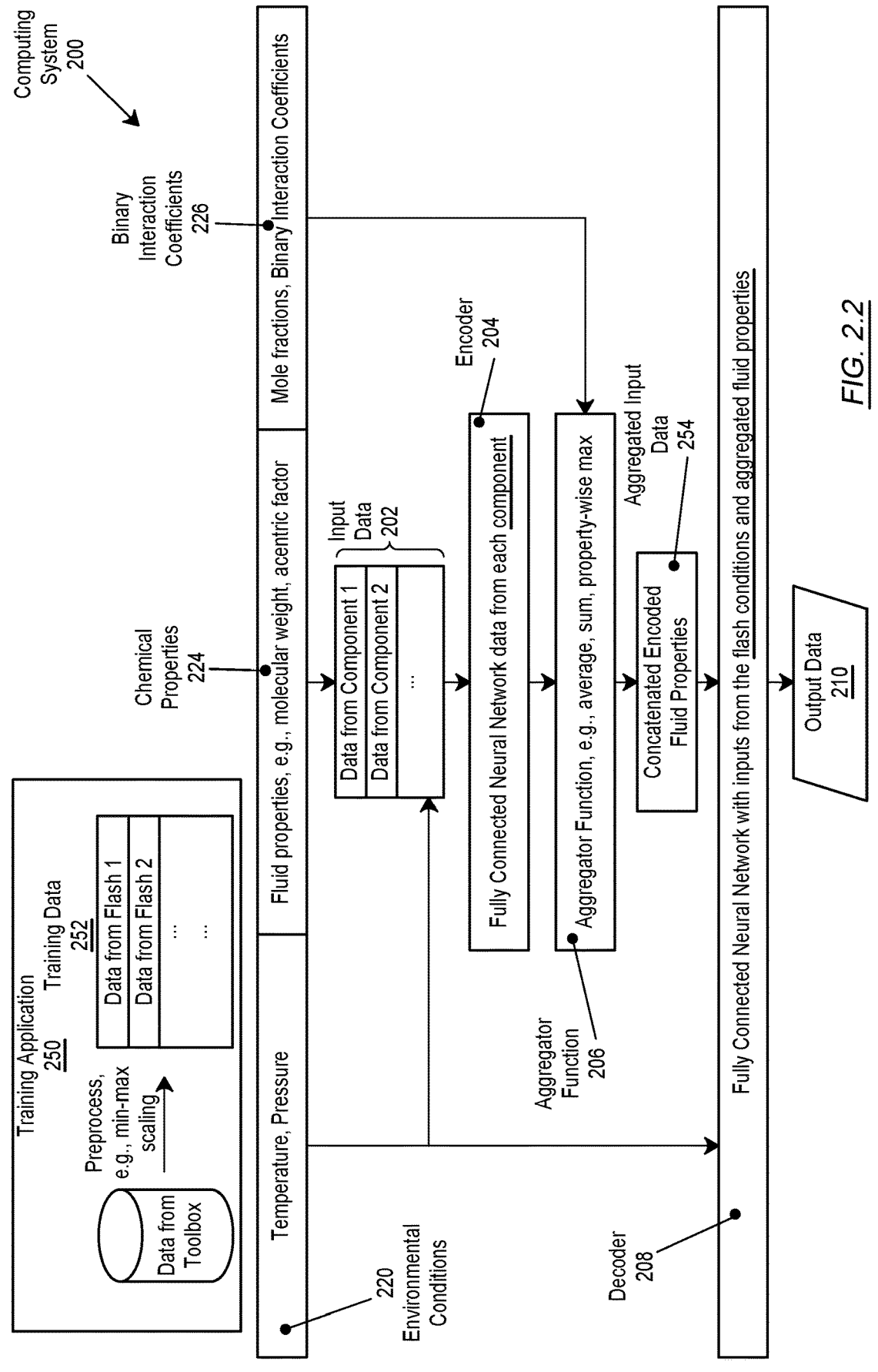
FIG. 2.2

Chemical Properties A
400A

| | Critical Temperature (K) | Critical Pressure (Pa) | Critical Volume (m3) | Molecular Weight | Acentric Factor | Omega A | Omega B | Volume Shift |
|---|---|---|---|---|---|---|---|---|
| Medium | 304.7 | 7386592.5 | 0.000094 | 44.01 | 0.225 | 0.488339 | 0.128722 | 0 |
| Heavy | 882 | 1104442.5 | 0.001354 | 416 | 0.941 | 0.437846 | 0.078791 | 0 |
| Light | 190.6 | 4604208 | 0.000098 | 16.043 | 0.013 | 0.468374 | 0.149893 | 0 |

FIG. 4.1

Encoder Output A
402A

| EOutput1 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| | 0.763 | 2.780 | 0.977 | 1.300 | 1.882 | 0.233 | 0.638 | 1.282 | 0.921 | 0.633 | 2.687 | 2.444 | 0.041 | 0.273 | 1.056 | 0.01 |

| EOutput2 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| | 0.121 | 4.907 | 2.350 | 3.222 | 0.481 | 0.221 | 0.435 | 1.371 | 1.290 | 0.166 | 6.050 | 4.979 | 0.026 | 2.008 | 2.450 | 0.020 |

Encoder Output B
402B

| EOutput3 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| | 0.027 | 3.834 | 1.889 | 2.499 | 0.117 | 0.343 | 0.298 | 0.772 | 1.020 | 0.081 | 4.718 | 3.882 | 0.064 | 0.118 | 1.924 | 0.17 |

402C
Encoder Output C

FIG. 4.2

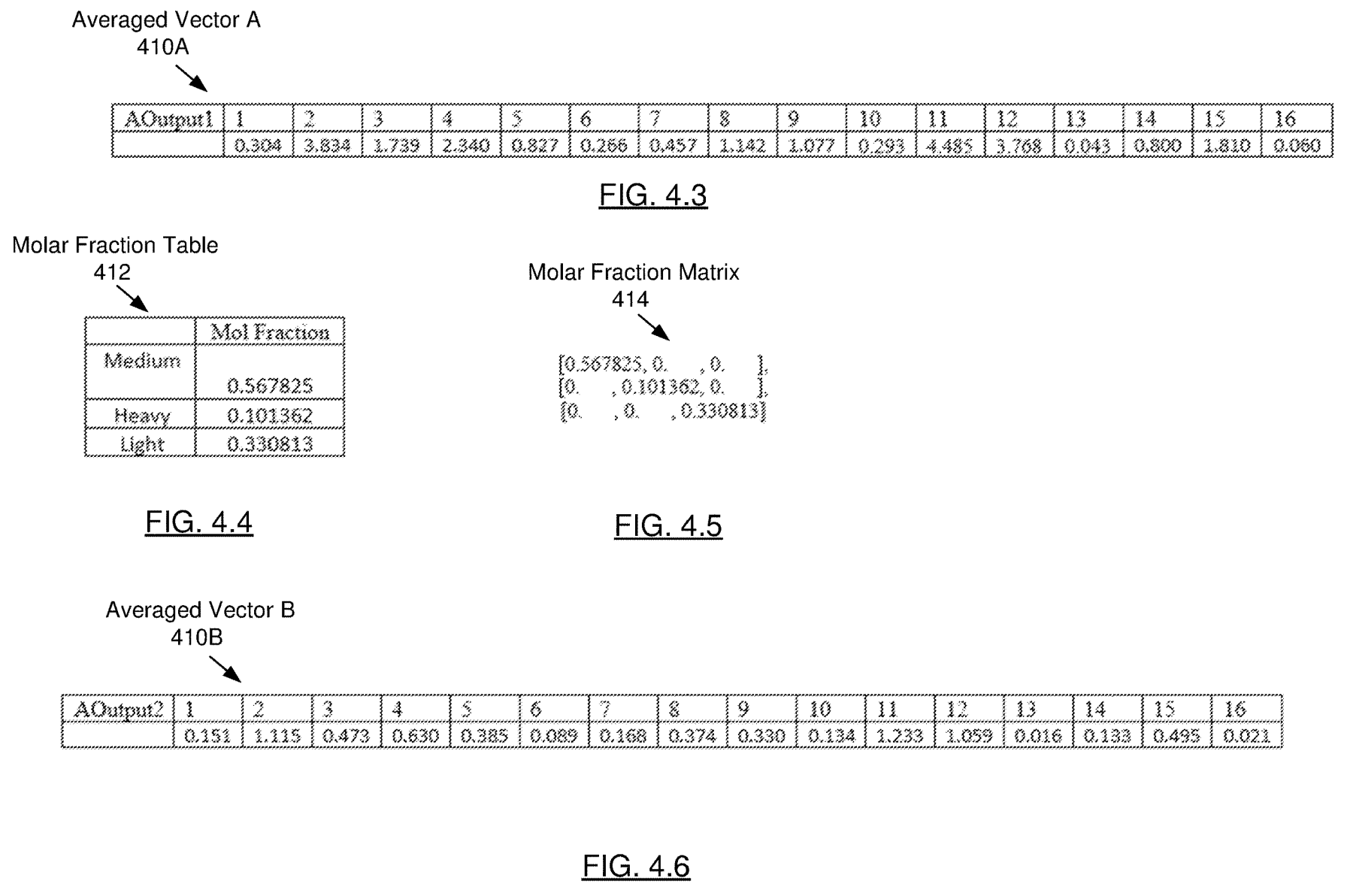

Averaged Vector A
410A

| AOutput1 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| | 0.204 | 3.834 | 1.739 | 2.340 | 0.827 | 0.266 | 0.457 | 1.142 | 1.077 | 0.293 | 4.485 | 3.768 | 0.043 | 0.800 | 1.810 | 0.080 |

FIG. 4.3

Molar Fraction Table
412

| | Mol Fraction |
|---|---|
| Medium | 0.567825 |
| Heavy | 0.101362 |
| Light | 0.330813 |

FIG. 4.4

Molar Fraction Matrix
414

Averaged Vector B
410B

| AOutput2 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| | 0.151 | 1.115 | 0.473 | 0.630 | 0.385 | 0.089 | 0.168 | 0.374 | 0.330 | 0.134 | 1.233 | 1.059 | 0.016 | 0.133 | 0.495 | 0.021 |

FIG. 4.6

Binary Interaction Coefficients
422

| | Medium | Heavy | Light |
|---|---|---|---|
| Medium | 0 | 0 | 0 |
| Heavy | 0.009023 | 0 | 0 |
| Light | -0.026562 | 0.193751 | 0 |

FIG. 4.7

Averaged Vector C
410C

| AOutput3 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| | 0.002 | 0.023 | 0.012 | 0.017 | 0.003 | 0.001 | 0.001 | 0.005 | 0.005 | 0.001 | 0.031 | 0.024 | 0.000 | 0.012 | 0.013 | 0.000 |

FIG. 4.8

Chemical Properties B
400B

| | Critical Temperature (K) | Critical Pressure (Pa) | Critical Volume (m3) | Molecular Weight | Acentric Factor | Omega A | Omega B | Volume Shift |
|---|---|---|---|---|---|---|---|---|
| Benzene | 562.1 | 4924395 | 0.000259 | 78.11 | 0.215 | 0.45723553 | 0.07779607 | -0.2922 |
| Light | 190.6 | 4604208 | 0.000098 | 16.043 | 0.013 | 0.468374 | 0.149893 | 0 |
| Medium | 304.7 | 7386592.5 | 0.000094 | 44.01 | 0.225 | 0.488339 | 0.128722 | 0 |
| Heavy | 882 | 1104442.5 | 0.001354 | 416 | 0.941 | 0.437846 | 0.078791 | 0 |

FIG. 4.9

500
Computing
System
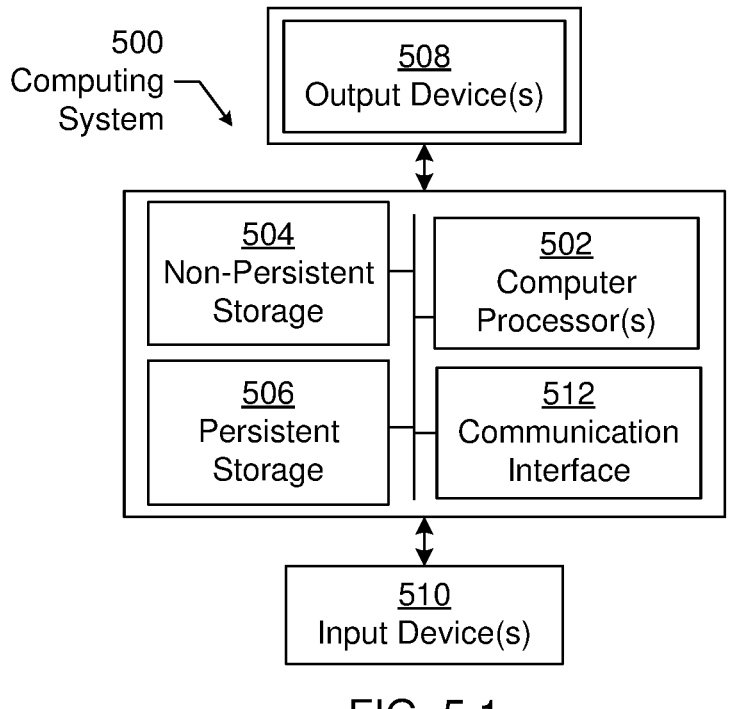
508
Output Device(s)
504
Non-Persistent
Storage
502
Computer
Processor(s)
506
Persistent
Storage
512
Communication
Interface
510
Input Device(s)
FIG. 5.1
520
Network
522
Node X
524
Node Y
526
Client Device
FIG. 5.2

GENERALIZABLE MACHINE LEARNING ALGORITHMS FOR FLASH CALCULATIONS

CROSS-REFERENCE TO RELATED APPLICATION

This application is a National Stage Entry of International Application No. PCT/US2021/071444, filed Sep. 14, 2021, which claims benefit under 35 U.S.C. § 119(e) to U.S. Provisional Patent Application Ser. No. 62/706,922, filed on Sep. 18, 2020, having the same inventors, and entitled "GENERALIZABLE MACHINE LEARNING ALGORITHMS FOR FLASH CALCULATIONS." U.S. Provisional Patent Application Ser. No. 62/706,922 is incorporated herein by reference in its entirety.

BACKGROUND

Flash calculations determine how much vapor and liquid result when petroleum is suddenly subjected ("flashed") to a given pressure and temperature. The resulting gas and oil depend on the chemical composition of the feed and the environmental conditions.

Traditional classical models often use cubic 'equations-of-state' tuned to match laboratory tests. These tuned equations are then used to predict the behavior of the petroleum in response to changing pressure and temperature conditions. However, the equations often utilize iterative and computationally expensive techniques to solve. Called millions of times, flash calculations are used in many industry activities where the fluid properties are needed. Flash calculations form a basis for major investment decisions through compositional reservoir simulation and facilities engineering. Unfortunately, with current computation techniques, reservoir and production engineers often simplify the equations in order to obtain results in practical amounts of time. This practice compromises accuracy and may impede collaboration when multiple 'models' are created for the same hydrocarbon mixture.

Traditional, fully-connected neural networks for flash calculations may be trained on fluids with a fixed number of chemical components, but do not work if the description is changed. The traditional methods fail to learn the relationships between the mixing components, and are unable to generalize beyond the fluids on which the model has been trained.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, one or more embodiments relate to a method including obtaining input data including an environmental condition and chemical properties of input components of an input fluid mixture, encoding, by an encoder machine learning model, the input data to obtain encoded input data, and receiving, by an aggregator function and from the encoder machine learning model, the encoded input data ordered in a sequence corresponding to an order of the input components. The method further includes aggregating, by the aggregator function, the encoded input data to obtain aggregated input data. The aggregated input data is independent of the sequence. The method further includes decoding, by a decoder machine learning model, the aggregated input data to obtain output data including a phase for an output mixture, and presenting the output data. Other aspects of the invention will be apparent from the following description and the appended claims.

BRIEF DESCRIPTION OF DRAWINGS

FIG. 2.1 and FIG. 2.2 show diagrams of a system in accordance with one or more embodiments.

FIGS. 4.1, 4.2, 4.3, 4.4, 4.5, 4.6, 4.7, 4.8, and 4.9 show examples in accordance with one or more embodiments.

FIGS. 5.1 and 5.2 show diagrams of a computing system in accordance with one or more embodiments.

DETAILED DESCRIPTION

Figure 1:
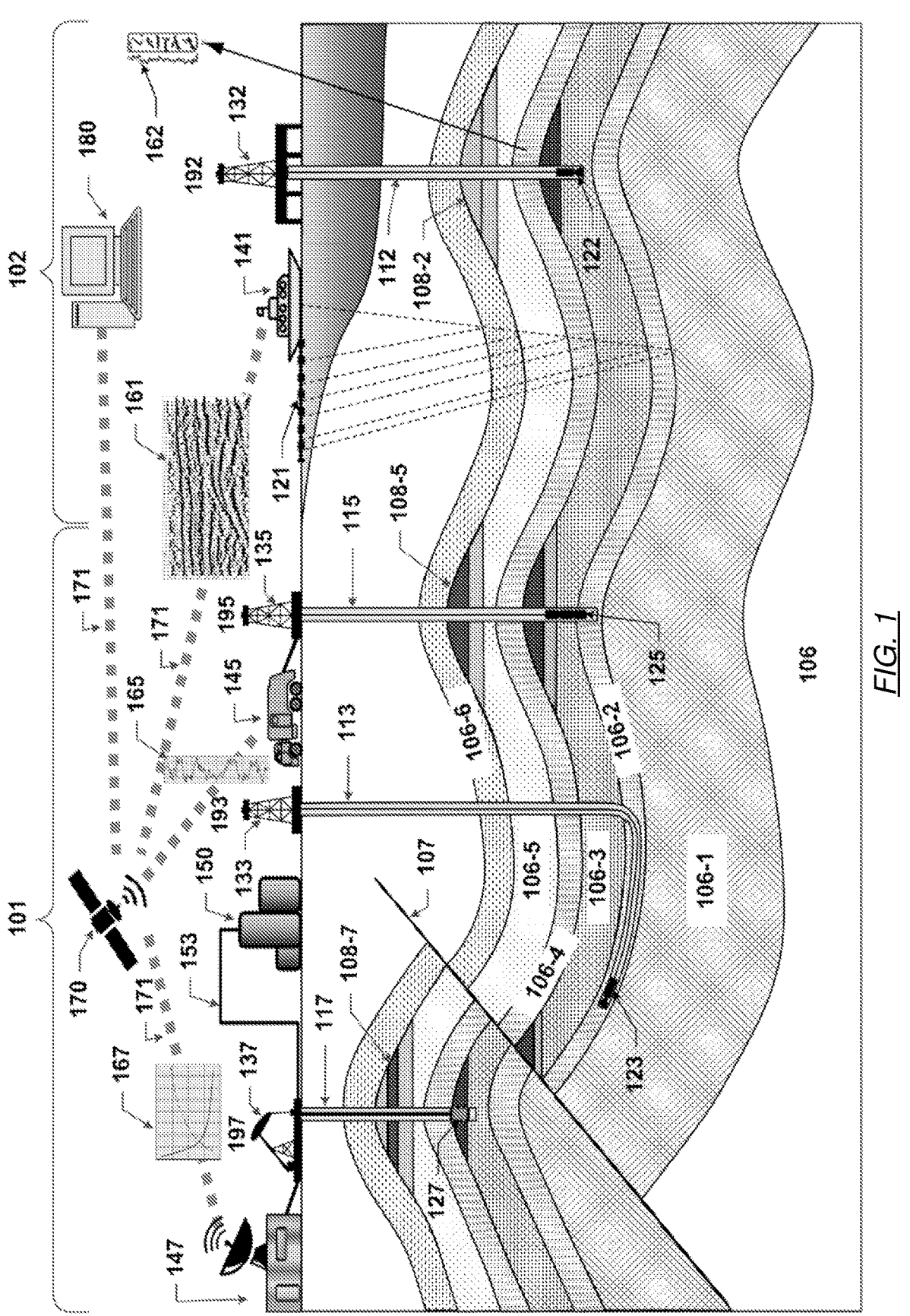
FIG. 1 shows a diagram of a field in accordance with one or more embodiments.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

The present disclosure is directed to machine learning algorithms for flash calculations. Input data including environmental conditions (e.g., pressure and temperature) and chemical properties of input components of an input fluid mixture is obtained. The input components are various hydrocarbon compounds, nitrogen, carbon dioxide, etc. The machine learning algorithms are generalizable to input fluid mixtures that include different numbers of input components.

The input data may include binary interaction coefficients that are adjustment factors representing pairwise interactions between components. Multiplying encoded input data by a matrix of binary interaction coefficients nonlinearly aggregates the pairwise interactions of the input components.

The input data is encoded by an encoder machine learning model (e.g., a fully connected neural network). The encoded input data is aggregated by an aggregator function to produce aggregated input data. The aggregator function is a set-permutation invariant function. Specifically, the output of the aggregator function is independent of the sequence in which the encoded input data is ordered and may handle an arbitrary count of encoded input. Examples of set-permutation invariant functions include calculating an average, sum, or mean of a set of values, and selecting a maximum value of a set of values. Leveraging a set-permutation invariant aggregator function circumvents the problem of generating different solutions when the ordering of input components is permuted, and when input components are added or removed.

A decoder machine learning model decodes the aggregated input data to obtain output data. The output data may include a binary classification that identifies one or more phases of an output mixture. The output data may include a regression that identifies the proportions (e.g., liquid/gas proportions) of the phase(s) of the output mixture. The output data may be used to set a parameter of an oilfield system. For example, the oilfield system may be a wellsite system, a wellbore, a well rig, etc.

FIG. 1 depicts a schematic view, partially in cross section, of an onshore field (101) and an offshore field (102) in which one or more embodiments may be implemented. In one or more embodiments, one or more of the modules and elements shown in FIG. 1 may be omitted, repeated, and/or substituted. Accordingly, embodiments should not be considered limited to the specific arrangement of modules shown in FIG. 1.

As shown in FIG. 1, the fields (101), (102) include a geologic sedimentary basin (106), wellsite systems (192), (193), (195), (197), wellbores (112), (113), (115), (117), data acquisition tools (121), (123), (125), (127), surface units (141), (145), (147), well rigs (132), (133), (135), production equipment (137), surface storage tanks (150), production pipelines (153), and an exploration and production (E&P) computer system (180) connected to the data acquisition tools (121), (123), (125), (127), through communication links (171) managed by a communication relay (170).

The geologic sedimentary basin (106) contains subterranean formations. As shown in FIG. 1, the subterranean formations may include several geological layers (106-1 through 106-6). As shown, the formation may include a basement layer (106-1), one or more shale layers (106-2, 106-4, 106-6), a limestone layer (106-3), a sandstone layer (106-5), and any other geological layer. A fault plane (107) may extend through the formations. In particular, the geologic sedimentary basin includes rock formations and may include at least one reservoir including fluids, for example the sandstone layer (106-5). In one or more embodiments, the rock formations include at least one seal rock, for example, the shale layer (106-6), which may act as a top seal. In one or more embodiments, the rock formations may include at least one source rock, for example the shale layer (106-4), which may act as a hydrocarbon generation source. The geologic sedimentary basin (106) may further contain hydrocarbon or other fluids accumulations associated with certain features of the subsurface formations. For example, accumulations (108-2), (108-5), and (108-7) associated with structural high areas of the reservoir layer (106-5) and containing gas, oil, water or any combination of these fluids.

In one or more embodiments, data acquisition tools (121), (123), (125), and (127), are positioned at various locations along the field (101) or field (102) for collecting data from the subterranean formations of the geologic sedimentary basin (106), referred to as survey or logging operations. In particular, various data acquisition tools are adapted to measure the formation and detect the physical properties of the rocks, subsurface formations, fluids contained within the rock matrix and the geological structures of the formation.

For example, data plots (161), (162), (165), and (167) are depicted along the fields (101) and (102) to demonstrate the data generated by the data acquisition tools. Specifically, the static data plot (161) is a seismic two-way response time. Static data plot (162) is core sample data measured from a core sample of any of subterranean formations (106-1 to 106-6). Static data plot (165) is a logging trace, referred to as a well log. Production decline curve or graph (167) is a dynamic data plot of the fluid flow rate over time. Other data may also be collected, such as historical data, analyst user inputs, economic information, and/or other measurement data and other parameters of interest.

The acquisition of data shown in FIG. 1 may be performed at various stages of planning a well. For example, during early exploration stages, seismic data (161) may be gathered from the surface to identify possible locations of hydrocarbons. The seismic data may be gathered using a seismic source that generates a controlled amount of seismic energy. In other words, the seismic source and corresponding sensors (121) are an example of a data acquisition tool. An example of seismic data acquisition tool is a seismic acquisition vessel (141) that generates and sends seismic waves below the surface of the earth. Sensors (121) and other equipment located at the field may include functionality to detect the resulting raw seismic signal and transmit raw seismic data to a surface unit (141). The resulting raw seismic data may include effects of seismic wave reflecting from the subterranean formations (106-1 to 106-6).

After gathering the seismic data and analyzing the seismic data, additional data acquisition tools may be employed to gather additional data. Data acquisition may be performed at various stages in the process. The data acquisition and corresponding analysis may be used to determine where and how to perform drilling, production, and completion operations to gather downhole hydrocarbons from the field. Generally, survey operations, wellbore operations and production operations are referred to as field operations of the field (101) or (102). These field operations may be performed as directed by the surface units (141), (145), (147). For example, the field operation equipment may be controlled by a field operation control signal that is sent from the surface unit.

Further as shown in FIG. 1, the fields (101) and (102) include one or more wellsite systems (192), (193), (195), and (197). A wellsite system is associated with a rig or a production equipment, a wellbore, and other wellsite equipment configured to perform wellbore operations, such as logging, drilling, fracturing, production, or other applicable operations. For example, the wellsite system (192) is associated with a rig (132), a wellbore (112), and drilling equipment to perform drilling operation (122). In one or more embodiments, a wellsite system may be connected to a production equipment. For example, the well system (197) is connected to the surface storage tank (150) through the fluids transport pipeline (153).

In one or more embodiments, the surface units (141), (145), and (147), are operatively coupled to the data acquisition tools (121), (123), (125), (127), and/or the wellsite systems (192), (193), (195), and (197). In particular, the surface unit is configured to send commands to the data acquisition tools and/or the wellsite systems and to receive data therefrom. In one or more embodiments, the surface units may be located at the wellsite system and/or remote locations. The surface units may be provided with computer facilities (e.g., an E&P computer system) for receiving, storing, processing, and/or analyzing data from the data acquisition tools, the wellsite systems, and/or other parts of the field (101) or (102). The surface unit may also be provided with, or have functionality for actuating, mechanisms of the wellsite system components. The surface unit may then send command signals to the wellsite system components in response to data received, stored, processed, and/or analyzed, for example, to control and/or optimize various field operations described above.

In one or more embodiments, the surface units (141), (145), and (147) are communicatively coupled to the E&P computer system (180) via the communication links (171). In one or more embodiments, the communication between the surface units and the E&P computer system may be managed through a communication relay (170). For example, a satellite, tower antenna or any other type of communication relay may be used to gather data from multiple surface units and transfer the data to a remote E&P computer system for further analysis. Generally, the E&P computer system is configured to analyze, model, control, optimize, or perform management tasks of the aforementioned field operations based on the data provided from the surface unit. In one or more embodiments, the E&P computer system (180) is provided with functionality for manipulating and analyzing the data, such as analyzing seismic data to determine locations of hydrocarbons in the geologic sedimentary basin (106) or performing simulation, planning, and optimization of E&P operations of the wellsite system. In one or more embodiments, the results generated by the E&P computer system may be displayed for user to view the results in a two-dimensional (2D) display, three-dimensional (3D) display, or other suitable displays. Although the surface units are shown as separate from the E&P computer system in FIG. 1, in other examples, the surface unit and the E&P computer system may also be combined.

In one or more embodiments, the E&P computer system (180) is implemented by an E&P services provider by deploying applications with a cloud based infrastructure. As an example, the applications may include a web application that is implemented and deployed on the cloud and is accessible from a browser. Users (e.g., external clients of third parties and internal clients of the E&P services provider) may log into the applications and execute the functionality provided by the applications to analyze and interpret data, including the data from the surface units (141), (145), and (147). The E&P computer system and/or surface unit may correspond to a computing system, such as the computing system shown in FIGS. 5.1 and 5.2 and described below.

FIG. 2.1 is a diagram of a computing system (200) in accordance with one or more embodiments of the disclosure. The computing system (200) may be a computing system such as described below with reference to FIGS. 5.1 and 5.2. For example, the computing system (200) may be the E&P computing system described in reference to FIG. 1. In one or more embodiments, the computing system (200) includes a repository (not shown). The repository may be any type of storage unit and/or device (e.g., a file system, database, collection of tables, or any other storage mechanism) for storing data. Further, the repository may include multiple different storage units and/or devices. The multiple different storage units and/or devices may or may not be of the same type or located at the same physical site.

As shown in FIG. 2.1, the computing system (200) includes input data (202), an encoder (204), an aggregator function (206), a decoder (208), and output data (210). The input data (202) and/or output data (210) may be stored in the repository. The input data (202) includes environmental conditions (220), input components (222) of an input fluid mixture, and/or binary interaction coefficients (226). The environmental conditions (220) are conditions under which a flash calculation may be performed on the input fluid mixture. For example, the environmental conditions (220) may include temperature, pressure, etc. The input components (222) are various hydrocarbon compounds, nitrogen, carbon dioxide, hydrogen sulfide, and/or other compounds or elements. The input fluid mixture is a combination of the input components (222). An input component (222) has one or more chemical properties (224). Examples of chemical properties (224) may include molecular weight, acentric factor, etc. The binary interaction coefficients (226) are adjustment factors that represent pairwise interactions between components. A binary interaction coefficient (226) corresponds to a pair of input components. The binary interaction coefficient (226) may describe a physical interaction between the pair of input components. The binary interaction coefficients (226) may be represented in an N-by-N matrix (e.g., a lower triangular matrix), where N is the number of input components of the input fluid mixture.

In one or more embodiments, the input data (202) includes the molar fractions of the input components in the input fluid mixture. The molar fractions of the input components may be arranged in a molar fraction matrix (e.g., for use in matrix multiplication, as described below).

The size of the input data (202) is a function of the number of input components (222), the number of environmental conditions (220), and the number of chemical properties (224). As an example, the size of the input data (202) may be proportional to $8*N+N!/(2*(N-2)!)$, where N is the number of input components (222).

The encoder (204) is configured to encode the input data (202). The encoder (204) includes functionality to send encoded input data to the aggregator function (206). The encoder (204) and the decoder (208) are deep learning machine learning models. Deep learning, also known as deep structured learning or hierarchical learning, is part of a broader family of machine learning methods based on learning data representations, as opposed to task-specific algorithms. The encoder and the decoder may be neural networks, such as a gated recurrent network (GRU), and recurrent neural networks (RNN). In other words, the system may have two neural networks, one for the encoder and one for the decoder.

A GRU and a RNN are networks that operate on a sequence and uses its own output as input for subsequent steps. The GRU and RNN may be one or more layers. Further, the GRU or RNN may be a long short-term memory (LSTM) network. The expression long short-term refers to the fact that LSTM is a model for the short-term memory which can last for a long period of time. LSTM units are the building blocks of the layers of the neural network in one or more embodiments.

As an example, the encoder (204) may initially include 5 fully connected neural network layers, with the following numbers of nodes in layers 1 thru 5: 16, 64, 256, 64, 16. The encoder (204) may leverage high performance computing, such that a library of chemicals and mixtures may be built on a cloud computing system to create a fluid modelling platform.

The encoder (204) may encode the input data (202) as a context vector. The context vector is a vector representation of the input data (202). The context vector is a hidden state of the encoder and encodes the meaning behind the input data (202). The contextual meaning is represented with numeric values in the context vector. In one or more embodiments, the context vector has fixed dimensionality. The size of the context vector is independent of the length of the input data (202) being encoded. In one or more embodiments, context vector is a numeric sequence.

The decoder (208) may generate the output data (210) from the context vector. The output data (210) may include the number of phases predicted such as liquid and gas, the relative amounts of those phases, the quantities of the chemical components in the phases and/or the physical properties of the phases such as density, viscosity, etc.

The aggregator function (206) includes functionality compute a set-permutation invariant aggregator function. A set-permutation invariant function is a function f receiving a set of inputs $S=\{s_1, s_2, \ldots, s_N\}$, such that for any permutation P on the set of inputs S, the function f satisfies the following: $f(\{s_1, s_2, \ldots, s_N\})=\{s_{P(1)}, s_{P(2)}, \ldots, s_{P(N)}\}$. In other words, the result of applying a set-permutation invariant function is the same regardless of the order of the inputs to the set-permutation invariant function. As a simple example, if f is a set-permutation invariant function, then $f(a, b, c)=f(b, a, c)=f(c, a, b)$, etc. Examples of set-permutation invariant functions include selecting a maximum value of a set of values, calculating an average, sum, or mean of a set of values (e.g., values of environmental conditions (220) or chemical properties (224)), etc. Continuing this example, the aggregator function may weight an average of its inputs by molar fraction and be able to process both small and large counts of components.

Turning to FIG. 2.2, the aggregator function (206) includes functionality to send aggregated input data (254) to the decoder (208). The aggregated input data (254) represents the aggregation of the encoded input data through the application of the aggregator function. The aggregated input data (254) may be stored in the repository.

Like the encoder (204), the decoder (208) may be a deep learning machine learning model. As an example, the decoder (208) may initially include 5 fully connected neural network layers, with the following numbers of nodes in layers 1 thru 5: 16, 64, 256, 64, 2. The decoder (208) may be configured to decode the aggregated input data (254) into output data (210). Returning to FIG. 2.1, the output data (210) includes phases (234) of an output mixture. The phase (234) may be a state of matter (e.g., gaseous, fluid, or solid).

The decoder (208) may perform a binary classification task that identifies the phases (234) of an output mixture. The decoder (208) may also perform a regression task that identifies the proportions (e.g., fluid/gas proportions) of the phases (234) for the output mixture and properties of the phases. In a scenario where the decoder (208) performs both the binary classification task and the regression task, the next to final layer of the neural network of the decoder (208) may increase in size, with part of the neurons contributing to the binary classification task and part of the neurons contributing to the regression task. The decoder (208) may predict physical parameters for the output mixture, such as density, viscosity, etc. The decoder output, combined with the encoder outputs corresponding to the input components (222), may also be used to predict the proportions of the chemicals in the phases of the output mixture.

Returning to FIG. 2.2, the encoder (204) and/or the decoder (208) may be trained by a training application (250) using training data (252). The training application (250) is a collection of programs that may execute on the computing system (200). The training data (252) may include, for input components of different input fluid mixtures, training input data including environmental conditions and chemical properties of the input components. The training input data may be labeled with corresponding training output data including one or more phases for output mixtures.

The encoder (204) and the decoder (208) may be trained together to jointly optimize both machine learning models. For example, the weights and/or biases of the encoder (204) and the decoder (208) may be changed at the same time to minimize a combined loss function that combines a loss function of the encoder and a loss function of the decoder. Continuing this example, the combined loss function may be minimized during the training of the encoder (204) and the decoder (208). The loss function may include a mismatch from pre-calculated data from the cubic equation of state, as well as physics based terms such as fugacity. The training data (252) may have the same structure as the input data (202). The training data (252) may be stored in the repository.

The training data (252) may be pre-processed by normalizing the training data (252). For example, the values in the training data (252) may be normalized in order to keep the values substantially equivalent in magnitude. Normalization may also enable the features (e.g., environmental conditions or chemical properties) to be treated equally. The values may be normalized based on known values (e.g., known maximum or upper bounds) for the feature. For example, when an upper or lower bound of an environmental condition (e.g., temperature or pressure) is known, the environmental condition may be normalized using the upper or lower bound of the environmental condition. Continuing this example, the upper or lower bound may be based on the output from another machine learning model that predicts the upper or lower bound. As another example, a static value may be used for normalization (e.g., based on general reservoir values).

The output data (210) may include the results of the aforementioned binary classification, the regression, and/or prediction tasks performed by the decoder (208). As an example, the output data may include two hydrocarbon phases (e.g., one gas phase and one fluid phase) or one hydrocarbon phase (e.g., either one gas phase or one fluid phase). As another example, the output data may include two immiscible fluid phases plus a gas phase, for a total of three hydrocarbon phases.

While FIG. 2.1 and FIG. 2.2 show a configuration of components, other configurations may be used without departing from the scope of the disclosure. For example, various components may be combined ("lumped") in a single component. As another example, the functionality performed by a single component may be performed by two or more components.

Figure 3:
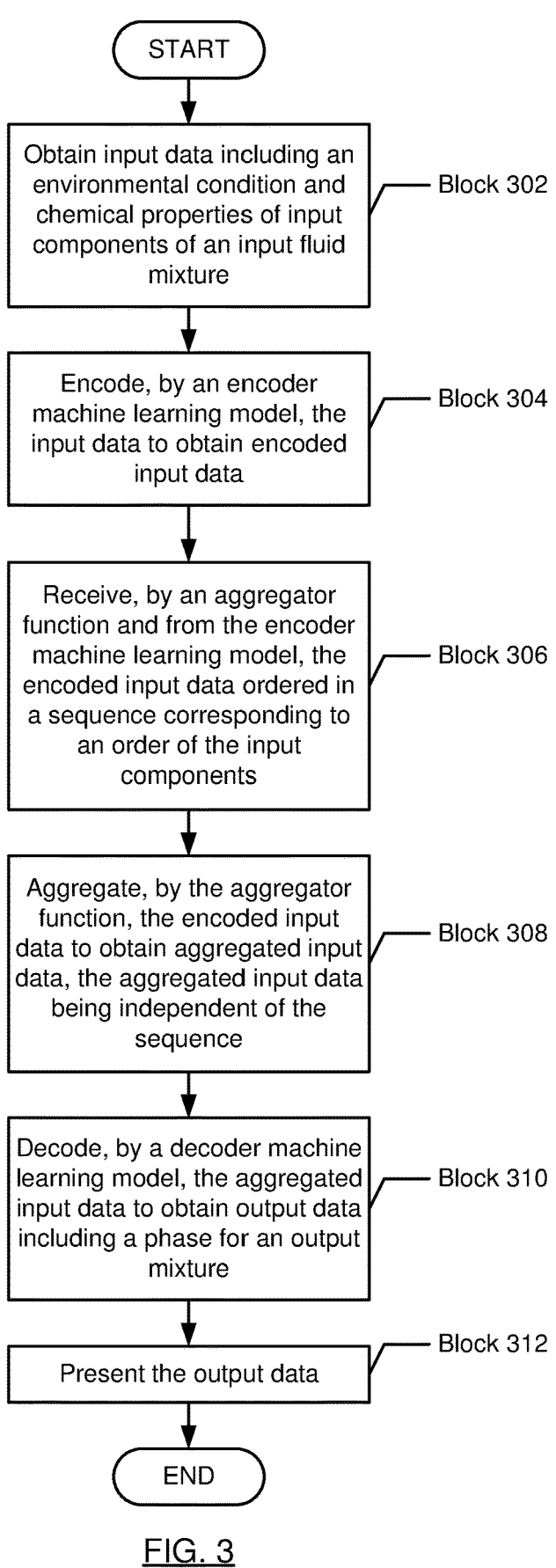
FIG. 3 shows a flowchart in accordance with one or more embodiments.

FIG. 3 shows a flowchart in accordance with one or more embodiments of the disclosure. The flowchart depicts a process for learning a flash computation. One or more of the blocks in FIG. 3 may be performed by the components (e.g., the encoder (204), the aggregator function (206), and the decoder (208) of the computing system (200)) discussed above in reference to FIG. 2.1 and FIG. 2.2. In one or more embodiments, one or more of the blocks shown in FIG. 3 may be omitted, repeated, and/or performed in parallel, or in a different order than the order shown in FIG. 3. Accordingly, the scope of the disclosure should not be considered limited to the specific arrangement of blocks shown in FIG. 3.

Initially, in Block 302, input data including an environmental condition and chemical properties for input components of an input fluid mixture are obtained. For example, one or more environmental conditions may be obtained using various sensors, such as temperature sensors, pressure sensors, etc.

In one or more embodiments, the input data includes binary interaction coefficients. The binary interaction coefficients may be obtained by analyzing historical data on input fluid mixtures whose components are also included in the input components. For example, the historical data may be obtained from the output of various tools, such as previous laboratory or subsurface tests. In one or more embodiments, the input data includes the molar fractions of the input components in the input fluid mixture.

In Block 304, the input data is encoded, by an encoder machine learning model, to obtain encoded input data. The encoder may be configured to generate one or more context vectors from the input data. A context vector may include a hidden state of the encoder. The hidden state may correspond to an input component. The encoded input values when stacked, may form a matrix whose dimensions are N-by-m, where m is the output size of the encoder, and where N is the number of input components of the input fluid mixture. The encoder may encode the input components according to an order (e.g., a sequence) of the input components. That is, if the input components include components A, B, and C, then the encoder may encode the input components in any of the following orders: 1) A, B, C; 2) A, C, B; 3) B, A, C; or 4) B, C, A.

In Block 306, the encoded input data is received, by an aggregator function and from the encoder machine learning model, ordered in a sequence corresponding to an order of the input components. For example, the order of the input components may be the order in which the input components are encoded by the encoder machine learning model.

In Block 308, the encoded input data is aggregated by the aggregator function to obtain aggregated input data. The aggregated input data is independent of the sequence and can scale to an arbitrary number of input components. For example, the aggregator function is a set-permutation invariant function whose output is independent of any ordering or sequence of its inputs. Examples of set-permutation invariant functions include selecting a maximum value of a set of values, and calculating an average, sum, or mean of a set of values.

The aggregator function may perform one or more calculations on the encoded input data (e.g., the context vector) to obtain the aggregated input data. As one example, the aggregated input data may include a first aggregated (e.g., an averaged) vector calculated from individual vectors corresponding to the input components. Continuing this example, FIG. 4.3 shows averaged vector A (410A) calculated as an average of encoder outputs (402A, 402B, 402C) that correspond to input components of an input fluid mixture.

When the binary interaction coefficients are present, the aggregated input data may include a second aggregated vector calculated using the binary interaction coefficients. For example, the aggregator function may combine the encoded input data with the binary interaction coefficients. The aggregator function may multiply the encoded input data by the binary interaction coefficients represented as a matrix. The dimensions of the aggregated matrix resulting from multiplying the encoded input data and the binary interaction coefficients matrix are N-by-m, where m is the output size of the encoder, and where N is the number of input components. Multiplying the encoded input data and the binary interaction coefficients nonlinearly aggregates the pairwise interactions of the input components while preserving the set-permutation invariance property of the aggregator function. The resulting aggregated matrix may be transformed to a second aggregated vector by averaging the values of the rows in the aggregated matrix. The aggregated input data may include both the first aggregated vector and the second aggregated vector. For example, the aggregated input data may be the concatenation of the first aggregated vector and the second aggregated vector.

The aggregator function may combine the encoded input data with the molar fractions of the input components. Continuing the above example, the molar fractions of the input components (e.g., represented as a diagonal matrix) may be multiplied with the encoded input data. Further continuing the above example, the molar fractions of the input components are shown as a molar fraction matrix (414) in FIG. 4.5, which is multiplied with the encoded input data of FIG. 4.2.

The aggregator function sends the aggregated input data to the decoder.

In Block 310, the aggregated input data is decoded, by a decoder machine learning model, to obtain output data. The output data may include a binary classification that identifies one or more phases for an output mixture. The output data may include a regression that identifies the proportions (e.g., liquid/gas proportions) of the phase(s) of the output mixture. In other words, the output data may identify the fluid/gas proportions for the output mixture. The output data may include, for the output mixture, physical parameters such as density, viscosity, etc.

In Block 312, the output data is presented. For example, the output data may be presented to a user of a computing system via a user interface. The output data may be used to set a parameter of an oilfield system. For example, the oilfield system may be a wellsite system, a wellbore, a well rig, production equipment, drilling equipment, a production pipeline, etc. The output data may be used to set a parameter of a simulation of an oilfield system and for the engineering design of well, pipeline and facilities infrastructure.

FIG. 4.1, FIG. 4.2, FIG. 4.3, FIG. 4.4, FIG. 4.5, FIG. 4.6, FIG. 4.7, FIG. 4.8, and FIG. 4.9 show implementation examples in accordance with one or more embodiments. The implementation examples are for explanatory purposes and not intended to limit the scope of the disclosure. One skilled in the art will appreciate that implementation of embodiments of the disclosure may take various forms and still be within the scope of the disclosure.

In particular, FIG. 4.1 shows a table of chemical properties (400A) ((224) in FIG. 2.1 and FIG. 2.2)) of three input components of an initial input fluid mixture: Hydrocarbon Medium, Hydrocarbon Heavy, and Hydrocarbon Light. A row from the table of chemical properties (400A) is normalized (relative to commonly used values) and then encoded by the encoder. The input to the encoder includes the 8 properties in the table of chemical properties (400A), concatenated with normalized environmental conditions of the fluid mixture, for a total of 30 inputs for the three input components. The pre-normalized, environmental conditions example include a temperature of 340 degrees K and a pressure of 1E6 Pa.

The architecture of the encoder is a fully connected neural network, with 5 hidden layers having 16, 64, 256, 64 and 16 nodes respectively. As shown in FIG. 4.2, input data corresponding to the chemical properties of the Hydrocarbon Medium input component is encoded by the encoder network yielding encoder output A (402A), which has 16 output nodes (e.g., corresponding to the 16 nodes of the last layer of the encoder). Subsequently and independently, the chemical properties of the Hydrocarbon Heavy input component are encoded by the same encoder network yielding encoder output B (402B). Similarly, the chemical properties of the Hydrocarbon Light input component are encoded by the same encoder network yielding encoder output C (402C). This process may be repeated for any additional components that are present in the initial input fluid mixture. The encoder outputs (402A, 402B, 402C) are arranged in a matrix of 3 rows and 16 columns and then sent to the aggregator function.

The aggregator function calculates three averaged vectors, as described below. FIG. 4.3 shows averaged vector A (410A), calculated as a simple arithmetic average of the encoder outputs (402A, 402B, 402C). Averaged vector A (410A) is a single vector with 16 columns. The size of this vector is independent of the number of input components in the initial input fluid mixture. That is, averaged vector A (410A) represents averaged properties of the initial input fluid mixture rather than properties of individual components.

FIG. 4.4 shows a molar fraction table (412) for the three input components of the initial input fluid mixture. FIG. 4.5 shows a diagonal molar fraction matrix (414) that arranges the molar fraction values of the molar fraction table (412) for matrix multiplication. The molar fraction matrix (414) is multiplied with the encoder outputs (402A, 402B, 402C), yielding a 3×16 molar fraction encoded output matrix. The rows of the molar fraction encoded output matrix are then averaged over the three input components, yielding averaged vector B (410B), as shown in FIG. 4.6.

The molar fraction encoder output matrix is multiplied with the binary interaction coefficients (422) ((226) in FIG. 2.1 and FIG. 2.2)) of FIG. 4.7. The binary interaction coefficients (422) are adjustment factors in the range [−1, 1] corresponding to pairwise interactions between the three input components of the initial input fluid mixture. FIG. 4.7 shows that the binary interaction coefficients (422) are arranged in a lower diagonal matrix.

The result of multiplying the molar fraction encoder output matrix with the binary interaction coefficients (422) is averaged over the three input components, yielding averaged vector C (410C), which is a 1×16 vector, as shown in FIG. 4.8.

The three averaged vectors (410A, 410B, 410C), which are 1×16 vectors, are then concatenated with the normalized environmental conditions (temperature and pressure) of the initial input fluid mixture, yielding a 1×50 vector that is passed as aggregated input to the decoder. The decoder is a fully connected neural network with 5 hidden layers having 16, 64, 256, 64, and 2 nodes respectively. The last 2 nodes are the final output and include a prediction for the number of hydrocarbon phases (typically a single phase or two phases) and the fraction of moles found in the liquid phase. In this example, the output is [0.99979854, 0.109449]. The first quantity implies a very high confidence that the output mixture has two phases with a liquid fraction of ~10.9%. The 'ground truth' from the cubic equation of state algorithm is [1, 0.10666582].

FIG. 4.9 shows another table of chemical properties (400B) for four input components of a modified input fluid mixture: Benzene, Hydrocarbon Medium, Hydrocarbon Heavy, and Hydrocarbon Light. The modified input fluid mixture is the result of adding a small amount (e.g., a 5% molar fraction) of benzene to the initial input fluid mixture. The encoder is applied to the table of chemical properties (400B) without retraining the weights of the encoder or decoder. The binary interaction coefficients for the input components of the modified input fluid mixture remain as shown in FIG. 4.7, with the addition of new binary interaction coefficients of 0 between benzene and the other 3 input components. The input components of the modified input fluid mixture are processed similarly to the input components of the initial input fluid mixture. For example, the molar fraction table (412) of FIG. 4.4 is modified to include an entry for the new input component, benzene. In addition, the molar fraction matrix (414) of FIG. 4.5 is modified to include entries for the benzene input component, resulting in a 4×4 matrix. The output for the modified input fluid mixture is [0.9989384, 0.14325964], which is similar to the output for the initial input fluid mixture. This result is expected, as the modified input fluid mixture was obtained by making a small change to the initial input fluid mixture. The 'ground truth' for the modified input fluid mixture from the cubic equation of state algorithm is [1, 0.14001667].

Embodiments of the disclosure may be implemented on a computing system specifically designed to achieve an improved technological result. When implemented in a computing system, the features and elements of the disclosure provide a significant technological advancement over computing systems that do not implement the features and elements of the disclosure. Any combination of mobile, desktop, server, router, switch, embedded device, or other types of hardware may be improved by including the features and elements described in the disclosure. For example, as shown in FIG. 5.1, the computing system (500) may include one or more computer processors (502), non-persistent storage (504) (e.g., volatile memory, such as random access memory (RAM), cache memory), persistent storage (506) (e.g., a hard disk, an optical drive such as a compact disk (CD) drive or digital versatile disk (DVD) drive, a flash memory, etc.), a communication interface (512) (e.g., Bluetooth interface, infrared interface, network interface, optical interface, etc.), and numerous other elements and functionalities that implement the features and elements of the disclosure.

The computer processor(s) (502) may be an integrated circuit for processing instructions. For example, the computer processor(s) may be one or more cores or micro-cores of a processor. The computing system (500) may also include one or more input devices (510), such as a touchscreen, keyboard, mouse, microphone, touchpad, electronic pen, or any other type of input device.

The communication interface (512) may include an integrated circuit for connecting the computing system (500) to a network (not shown) (e.g., a local area network (LAN), a wide area network (WAN) such as the Internet, mobile network, or any other type of network) and/or to another device, such as another computing device.

Further, the computing system (500) may include one or more output devices (508), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (502), non-persistent storage (504), and persistent storage (506). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

The computing system (500) in FIG. 5.1 may be connected to or be a part of a network. For example, as shown in FIG. 5.2, the network (520) may include multiple nodes (e.g., node X (522), node Y (524)). A node may correspond to a computing system, such as the computing system shown in FIG. 5.1, or a group of nodes combined may correspond to the computing system shown in FIG. 5.1. By way of an example, embodiments of the disclosure may be implemented on a node of a distributed system that is connected to other nodes. By way of another example, embodiments of the disclosure may be implemented on a distributed computing system having multiple nodes, where a portion of the disclosure may be located on a different node within the distributed computing system. Further, one or more elements of the aforementioned computing system (500) may be located at a remote location and connected to the other elements over a network.

Although not shown in FIG. 5.2, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (522), node Y (524)) in the network (520) may be configured to provide services for a client device (526). For example, the nodes may be part of a cloud computing system. The nodes may include functionality to receive requests from the client device (526) and transmit responses to the client device (526). The client device (526) may be a computing system, such as the computing system shown in FIG. 5.1. Further, the client device (526) may include and/or perform all or a portion of one or more embodiments of the disclosure.

The computing system or group of computing systems described in FIGS. 5.1 and 5.2 may include functionality to perform a variety of operations disclosed herein. For example, the computing system(s) may perform communication between processes on the same or different systems. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the name and/or address associated with the first socket object. The client process then transmits the connection request to the server process. Depending on availability, the server process may accept the connection request, establishing a communication channel with the client process, or the server process, busy in handling other operations, may queue the connection request in a buffer until server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data. For example, the extraction may be performed as follows by the computing system in FIG. 5.1. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (having layers of nodes at different levels of detail-such as in nested packet headers or nested document sections). Then, the raw, unprocessed stream of data symbols is parsed, in the context of the organizing pattern, into a stream (or layered structure) of tokens (where a token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as eXtensible Markup Language (XML)).

The extracted data may be used for further processing by the computing system. For example, the computing system of FIG. 5.1, while performing one or more embodiments of the disclosure, may perform data comparison. Data comparison may be used to compare two or more data values (e.g., A, B). For example, one or more embodiments may determine whether A>B, A=B, A !=B, A<B, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, B may be subtracted from A (i.e., A−B), and the status flags may be read to determine if the result is positive (i.e., if A>B, then A−B>0). In one or more embodiments, B may be considered a threshold, and A is deemed to satisfy the threshold if A=B or if A>B, as determined using the ALU. In one or more embodiments of the disclosure, A and B may be vectors, and comparing A with B involves comparing the first element of vector A with the first element of vector B, the second element of vector A with the second element of vector B, etc. In one or more embodiments, if A and B are strings, the binary values of the strings may be compared.

The computing system in FIG. 5.1 may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 5.1 may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions present a few examples of functions performed by the computing system of FIG. 5.1 and the nodes and/or client device in FIG. 5.2. Other functions may be performed using one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited by the attached claims.

What is claimed is:

1. A method comprising:
   obtaining a first plurality of input data comprising an environmental condition and a first plurality of chemical properties of a first plurality of input components of an input fluid mixture;
   encoding, by an encoder machine learning model, the first plurality of input data to obtain a plurality of encoded input data;
   receiving, by an aggregator function and from the encoder machine learning model, the plurality of encoded input data ordered in a sequence corresponding to an order of the first plurality of input components;
   aggregating, by the aggregator function, the plurality of encoded input data to obtain a plurality of aggregated input data, the plurality of aggregated input data being independent of the sequence;
   decoding, by a decoder machine learning model, the plurality of aggregated input data to obtain a first plurality of output data comprising a phase for an output mixture;
   presenting the first plurality of output data;
   setting, via a surface unit, at least one of a density or viscosity of the output mixture based on the first plurality of output data; and
   outputting, via a production pipeline, the output mixture having the at least one of the density or the viscosity,
   wherein the aggregator function obtains the plurality of aggregated input data by combining the plurality of encoded input data with a plurality of interaction coefficients, the plurality of interaction coefficients corresponding to a plurality of pairs of the first plurality of input components.

2. The method of claim 1, wherein the plurality of encoded input data is represented as a vector, wherein the plurality of interaction coefficients is represented as a matrix, and wherein combining the plurality of encoded input data with the plurality of interaction coefficients comprises multiplying the vector by the matrix.

3. The method of claim 1, wherein an interaction coefficient of the plurality of interaction coefficients describes a physical interaction between input components in a pair of the plurality of pairs.

4. The method of claim 1, further comprising:
   obtaining training data comprising, for a second plurality of input components of a plurality of input fluid mixtures, a second plurality of input data comprising a plurality of environmental conditions and a second plurality of chemical properties of the second plurality of input components;

labeling the second plurality of input data with a second plurality of output data comprising a plurality of phases for a plurality of output mixtures; and
   training the encoder machine learning model and the decoder machine learning model using the training data.

5. The method of claim 4, further comprising:
   before training the encoder machine learning model and the decoder machine learning model, normalizing the second plurality of input data using a value of one of the plurality of environmental conditions to obtain a plurality of normalized input data.

6. The method of claim 1, wherein the encoder machine learning model corresponds to a first loss function, and wherein the decoder machine learning model corresponds to a second loss function, the method further comprising:
   jointly training the encoder machine learning model and the decoder machine learning model using a combined loss function, the combined loss function being a combination of the first loss function and the second loss function.

7. The method of claim 1, further comprising:
   setting a parameter of an oilfield system using the first plurality of output data, the oilfield system comprising at least one of a wellbore, a well rig, production equipment, or the production pipeline.

8. A system comprising:
   a computer processor;
   a repository configured to store, for a first plurality of input components of an input fluid mixture, a first plurality of input data comprising an environmental condition and a first plurality of chemical properties;
   an encoder machine learning model executing on the computer processor and configured to encode the first plurality of input data to obtain a plurality of encoded input data;
   an aggregator function executing on the computer processor and configured to:
      receive, from the encoder machine learning model, the plurality of encoded input data ordered in a sequence corresponding to an order of the first plurality of input components, and
      aggregate the plurality of encoded input data to obtain a plurality of aggregated input data, the plurality of aggregated input data being independent of the sequence;
   a decoder machine learning model executing on the computer processor and configured to decode the plurality of aggregated input data to obtain a first plurality of output data comprising a phase for an output mixture;
   a user interface executing on the computer processor and configured to present the first plurality of output data;
   set, via a surface unit, at least one of a density or viscosity of the output mixture based on the first plurality of output data; and
   output, via a production pipeline, the output mixture having the at least one of the density or the viscosity,
   wherein the aggregator function is further configured to obtain the plurality of aggregated input data by combining the plurality of encoded input data with a plurality of interaction coefficients, the plurality of interaction coefficients corresponding to a plurality of pairs of the first plurality of input components.

9. The system of claim 8, wherein the plurality of encoded input data is represented as a vector, wherein the plurality of interaction coefficients is represented as a matrix, and wherein the aggregator function is further configured to combine the plurality of encoded input data with the plurality of interaction coefficients by multiplying the vector by the matrix.

10. The system of claim 8, wherein an interaction coefficient of the plurality of interaction coefficients describes a physical interaction between input components in a pair of the plurality of pairs.

11. The system of claim 8, further comprising a training application configured to:

obtain training data comprising, for a second plurality of input components of a plurality of input fluid mixtures, a second plurality of input data comprising a plurality of environmental conditions and a second plurality of chemical properties of the second plurality of input components;

label the second plurality of input data with a second plurality of output data comprising a plurality of phases for a plurality of output mixtures; and train the encoder machine learning model and the decoder machine learning model using the training data.

12. The system of claim 11, wherein the training application is further configured to:

before training the encoder machine learning model and the decoder machine learning model, normalize the second plurality of input data using a value of one of the plurality of environmental conditions to obtain a plurality of normalized input data.

13. The system of claim 11, wherein the encoder machine learning model corresponds to a first loss function, and wherein the decoder machine learning model corresponds to a second loss function, and wherein the training application is further configured to:

jointly train the encoder machine learning model and the decoder machine learning model using a combined loss function, the combined loss function being a combination of the first loss function and the second loss function.

14. The system of claim 8, the surface unit being configured to:

set a parameter of an oilfield system using the first plurality of output data, the oilfield system comprising at least one of a wellsite system, a wellbore, a well rig, production equipment, or the production pipeline.

15. A non-transitory computer readable medium comprising instructions that, when executed by a computer processor, perform operations comprising:

obtaining a first plurality of input data comprising an environmental condition and a first plurality of chemical properties of a first plurality of input components of an input fluid mixture;

encoding, by an encoder machine learning model, the first plurality of input data to obtain a plurality of encoded input data;

receiving, by an aggregator function and from the encoder machine learning model, the plurality of encoded input data ordered in a sequence corresponding to an order of the first plurality of input components;

aggregating, by the aggregator function, the plurality of encoded input data to obtain a plurality of aggregated input data, the plurality of aggregated input data being independent of the sequence;

decoding, by a decoder machine learning model, the plurality of aggregated input data to obtain a first plurality of output data comprising a phase for an output mixture;

presenting the first plurality of output data;

setting at least one of a density or viscosity of the output mixture based on the first plurality of output data; and outputting the output mixture having the at least one of the density or the viscosity, wherein the aggregator function obtains the plurality of aggregated input data by combining the plurality of encoded input data with a plurality of interaction coefficients, the plurality of interaction coefficients corresponding to a plurality of pairs of the first plurality of input components.

16. The non-transitory computer readable medium of claim 15, wherein the plurality of encoded input data is represented as a vector, wherein the plurality of interaction coefficients is represented as a matrix, wherein combining the plurality of encoded input data with the plurality of interaction coefficients comprises multiplying the vector by the matrix, and wherein an interaction coefficient of the plurality of interaction coefficients describes a physical interaction between input components in a pair of the plurality of pairs.

17. The non-transitory computer readable medium of claim 15, wherein the operations further comprise:

setting a parameter of an oilfield system using the first plurality of output data, the oilfield system comprising at least one of a wellsite system, a wellbore, a well rig, production equipment, or a production pipeline.

* * * * *